United States Patent [19]

Frank et al.

[11] Patent Number: 4,608,278
[45] Date of Patent: Aug. 26, 1986

[54] SMALL PARTICLE FORMATION AND ENCAPSULATION

[75] Inventors: Sylvan G. Frank, Columbus, Ohio; Arne F. Brodin, Sodertalje, Sweden; Chih-Ming J. Chen, East Syracuse, N.Y.; Siriporn Panthuvanich, Columbus, Ohio

[73] Assignee: The Ohio State University Research Foundation, Columbus, Ohio

[21] Appl. No.: 621,132

[22] Filed: Jun. 15, 1984

Related U.S. Application Data

[63] Continuation-in-part of Ser. No. 506,599, Jun. 22, 1983, abandoned.

[51] Int. Cl.$^4$ .............................................. B01J 13/02
[52] U.S. Cl. ................................ 427/213.35; 252/303; 252/363.5; 424/33; 424/35; 424/37; 427/213.3; 427/213.32; 427/213.33; 427/213.36; 514/962; 514/965
[58] Field of Search ...................... 427/213.35, 213.36, 427/213.3; 424/33, 35, 37; 252/303, 363.5; 514/965

[56] References Cited

U.S. PATENT DOCUMENTS

| 3,043,782 | 7/1962 | Jensen | 427/213.35 |
| 3,242,051 | 3/1966 | Hiestand et al. | 264/4.3 X |
| 3,574,132 | 4/1971 | Mosier et al. | 424/37 X |

OTHER PUBLICATIONS

W. L. Chiou et al.: "Enhancement of Dissolution Rates of Poorly Water-Soluble Drugs by Crystallization in Aqueous Surfactant Solutions . . . ", *J. Pharm. Sci.*, 65, 1702–1704, (1976).

K. Ikeda et al.: "Micellar Interaction of Tetracycline Antibiotics", *Chem. Pharm. Bull.*, 25, 106701072, (1977).

V. K. LaMer et al.: "Theory Production and Mechanism of Formation of Monodispersed Hydrosols", *J. Amer. Chem. Soc.*, 72, 4847–4854, (1950).

P. L. Madan: "Microencapsulation: I. Phase Separation or Coacervation", *Drug Development and Industrial Pharmacy*, 4, 95–116, (1978).

P. L. Madan: "Microencapsulation: II. Interfacial Reactions", *Drug Development and Industrial Pharmacy*, 4, 289–304, (1978).

P. L. Madan: "Clofibrate Microcapsules: III. Mechanism of Release", *Drug Development and Industrial Pharmacy*, 6, 629–644, (1980).

H. P. Merckle et al.: "Preparation and In Vitro Evaluation of Cellulose Acetate Phthalate Coacervate Microcapsules", *J. Pharm. Sci.*, 62, 1444–1448, (1973).

A. S. Michaels et al.: "The Effect of Surface Active Agents on Crystal Growth Rate and Crystal Habit", *J. Phys. Chem.*, 64, 13–19, (1960).

G. I. Mukhayer et al.: "Interactions Between Large Organic Ions of Opposite Charge: VI. Coacervation . . . ", *J. Coll. and Int. Sci.*, 66, 110–117, (1978).

J. R. Nixon et al.: "The In Vitro Evaluation of Gelatin Coacervate Microcapsules", *J. Pharm. Pharmac.*, 23, 147S–155S, (1971).

O. Siddiqui et al.: "Physical Factors Affecting Microencapsulation by Simple Coacervation of Gelatin", *J. Pharm. Pharmacol.*, 35, 70–73, (1983).

Chih-Ming James Chen: "Production of Drugs in Small Particle Form", Dissertation, The Ohio State University, 1981.

*Primary Examiner*—Richard D. Lovering

[57] ABSTRACT

The present invention is concerned with the simultaneous formation and encapsulation of small particles from aqueous solutions of compounds whose solubility is greater at a first pH than at a second pH. The process is preferably used to prepare a readily soluble encapsulated pharmaceutically active compound.

10 Claims, No Drawings

SMALL PARTICULE FORMATION AND ENCAPSULATION

This application is a continuation-in-part of U.S. patent application Ser. No. 506,599 filed June 22, 1983 and now abandoned.

The present invention is concerned with the simultaneous formation and encapsulation of small particles from aqueous solutions of compounds whose solubility is greater at a first pH than at a second pH. The process is preferably used to prepare a readily soluble encapsulated pharmaceutically active compound.

BACKGROUND OF THE INVENTION

From a pharmaceutical point of view, the smaller the particle size of a relatively insoluble drug the greater is its rate of solution and as a rule, the greater is its bioavailability (J. H. Fincher, J. Pharm. Sci., 57, 1825 (1968)). To this end, small particles are conventionally formed by mechanical subdivision of bulk matter or by aggregation of small molecules or ions (D. J. Shaw, "Introduction to Colloid and Surface Chemistry", 3rd Ed., Butterworths, London, 1980, Chapter 1). The production and applications of microcapsules for medical and technical use have been extensively reviewed (L. A. Luzzi, J. Pharm. Sci., 59, 1367 (1970); A. Kondo, "Microcapsule Processing and Technology", Marcel Dekker, N.Y. (1979); J. E. Vandegaer, "Microencapsulation: Processes and Applications", Plenum Press, New York (1976); J. R. Nixon, "Microencapsulation", Marcel Dekker, New York (1976); J. A. Bakan and J. L. Anderson, in "The Theory and Practice of Industrial Pharmacy", Second Ed., (Ed. L. Lachman, et al.), Lea & Febiger, Philadelphia, 1976, p. 420; M. H. Gutcho, "Microcapsules and Microencapsulation Techniques", Noyes Data Corp., N.J., (1976)).

SUMMARY OF THE INVENTION

A method has now been found which involves the formation of small core particles of a compound from solution and the concurrent encapsulation of the core particles in a coacervate of the encapsulating material as the pH of the system is altered. This process of encapsulation in a natural or synthetic polymer protects and stabilizes the active core compound. The new method for encapsulating weakly acidic or weakly basic organic compounds whose solubility in water decreases from a first pH to a second pH which comprises:

(a) dissolving said compound in the case of a weakly acidic compound in water in the presence of sufficient base to raise the pH to said first pH and at least 2 pH units above the pKa of the compound; and in the case of a weakly basic compound dissolving the compound in water in the presence of sufficient acid to lower the pH to said first pH and at least 2 pH units below the pKa of the compound; together with an encapsulating material and an electrolyte which is effective (but present in an amount just insufficient) to cause coacervation of the encapsulating material without interacting with it; and (b) stirring and titrating the solution with an acid or basic titrant effective to raise or lower the pH of said solution to said second pH to cause the concurrent precipitation of the compound as small particles and formation of a coacervate of the encapsulating material; and (c) gelling the encapsulating material.

In this process coacervation of the encapsulating material is believed to result from the addition of the acid or base during titration step (b), which amounts to sufficient additional electrolyte, when taken together with the electrolyte initially present to cause coacervation.

In an alternate embodiment, a suitable wetting agent or surfactant such as cetyltrimethylammonium bromide or sodium lauryl sulfate may also be used in step (a) of this process and the pH should be adjusted above or below the pKa depending on whether the compound is weakly acidic or basic, preferably at least 2 pH units below or above the pKa.

Suitable pharmaceutically active compounds whose solubility in water decreases at a first pH to a second pH are, for example, bacampicillin, griseofulvin, indomethacin, sodium sulfadiazine, erythromycin, theophylline, salicylic acid, acetylsalicylic acid, chlorzoxazone, lidocaine and alaproclate.

A suitable encapsulating material which will form a coacervate is, for example, gelatin (preferably of the type B; acid processed), methylcellulose, sodium carboxymethylcellulose, cellulose acetate phthalate and polyvinylpyrrolidone. A suitable electrolyte which is effective to cause coacervation of the encapsulating material without interacting with it is, for example, sodium sulfate solution, preferably a 5–30% aqueous solution which may also contain a suitable cosolvent, for example, an alcohol at about 0–10%. The compound, encapsulating material, wetting agent and electrolyte can be combined in step (a) in ratios of about (0.1–6):(0.1–4):(0.1–10):(0.4–48).

If the compound is weakly acidic, the titration in step (b) can be carried out, for example, with hydrochloric acid or acetic acid to a pH of about 4.3–4.5. If the compound is basic, sodium or potassium hydroxide can be used to a pH of about 8–10. If necessary, the temperature can be adjusted during the titration. The gelling of the encapsulating material can be achieved by treatment of the encapsulating material with cold (5° C.) $Na_2SO_4$ solution. If polyvinylpyrrolidone is used as the encapsulating material gelling can also be achieved by a number of other methods, for example:

1. application of heat (to 60° C.);
2. addition of hydrochloric acid, 0.05N–1.0N (10 ml 0.1M HCl/ml) to the mixture to be gelled;
3. application of heat (40°–45° C.) plus addition of sodium sulfate solution;
4. application of heat plus addition of hydrochloric acid;
5. application of heat (40°–45° C.) plus addition of hydrochloric acid and sodium sulfate.

Once formed, the microcapsules can be collected by conventional means, for instance, by centrifugation. The encapsulated particles formed by this process are less than 100 $\mu$m, preferably less than 10 $\mu$m; and the core particles are less than 25 $\mu$m, preferably less than 1 $\mu$m.

DETAILED DESCRIPTION OF THE INVENTION

According to one embodiment, the process comprises the following steps which are carried out at a temperature above 35° C., preferably 40°–45° C.

(a) dissolving a suitable pharmaceutically active compound in a solution of sodium sulfate containing ethyl alcohol, or another similar water miscible higher alcohols, for example, propanol or butanol;

(b) adding a gelatin solution to the solution from step a; and (c) titrating the solution obtained in step (b) with a suitable acid or base titrant while keeping the solution under constant agitation which results in a suspension of encapsulated pharmaceutically active small particles and coacervation of the gelatin.

The suspension is then poured into cold sodium sulfate solution and stirred at the temperature of an ice bath. This procedure causes "hardening" of the liquid gelatin shell of the microcapsules. The microcapsules are then collected, for instance, by centrifugation. The ratio of pharmaceutically active compound to sodium sulfate to ethyl alcohol is, for example, 1:7:1. The gelatin solution should preferably be prepared from type B (acid processed) gelatin, and of a pharmaceutical grade. The gelatin should be added as a 2–10% (w/w) solution, preferably a 5% (w/w) solution.

EXAMPLE 1

An aqueous solution consisting of 0.5 g sodium sulfadiazine, 0.5 ml ethyl alcohol, 13 ml of 20% sodium sulfate and 20 ml of 5% gelatin (type B: acid processed) was titrated, while under constant agitation with a magnetic stirrer, with 18.4 ml of 0.1N hydrochloric acid solution. This procedure resulted in a white suspension of microencapsulated sulfadiazine particles. The suspension was then stirred for an additional 15 minutes, following which it was poured into 200 ml of cold (5° C.) 7% sodium sulfate solution, and stirred for 30 minutes at ice-bath temperature. This procedure caused gelling of the liquid gelatin shell of the microcapsules. The entire process was monitored by observation of samples in the optical microscope. The microcapsules were of assymetric appearance and of a size less than 10 μm.

A schematic diagram of the preparation of the microcapsules according to Example 1 is illustrated below:

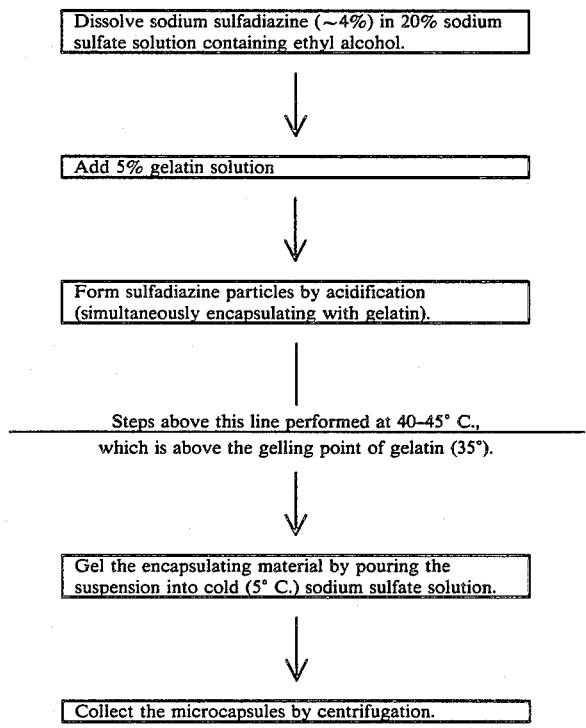

According to a second embodiment of the invention, the process comprises the following steps which are carried out at 40°–45° C.

(a) mixing solutions of a suitable pharmaceutically active compound, cetyltrimethylammonium bromide and gelatin;

(b) adding a sodium sulfate solution to the mixture obtained in step a; and (c) titrating the solution, obtained in step b with a suitable acid or base titrant while keeping the solution under constant agitation which results in a suspension of encapsulated pharmaceutically active small particles and coacervation of the gelatin.

The suspension from step c is then poured into a cold sodium sulfate solution and stirred at the temperature of an ice bath. This procedure causes "hardening" of the liquid gelatin shell of the microcapsules. The microcapsules are then collected, for instance, by centrifugation.

The ratio of pharmaceutically active compounds to cetyltrimethylammonium bromide to gelatin is about 1:0.1:2. The sodium sulfate solution is preferably a 20% aqueous solution of sodium sulfate.

EXAMPLE 2

An aqueous solution consisting of 10 ml of 0.1N sodium sulfadiazine (27.2 g/l), 1 ml of 10% cetyltrimethylammonium bromide and 10 ml of 10% gelatin (type B: acid processed) was mixed and maintained at 40°–45° C. under constant agitation (medium speed) with a magnetic stirrer for 3 minutes. With constant stirring, 12 ml of 20% sodium sulfate solution was added and mixing continued for another 3 minute period. The stirring rate was increased and 10 ml of 0.1M HCl was added from a fully opened buret. The resulting white suspension of microencapsulated sulfadiazine was stirred for an additional 10 minutes. The microcapsules were "hardened" by pouring the suspensions into 200 ml of cold (5° C.) 7% sodium sulfate solution and stirred at medium speed for 30 minutes at ice-bath temperature. According to microscopic inspection, the microcapsules were of a size less than 10 μm.

The procedure is further outlined in the diagram below:

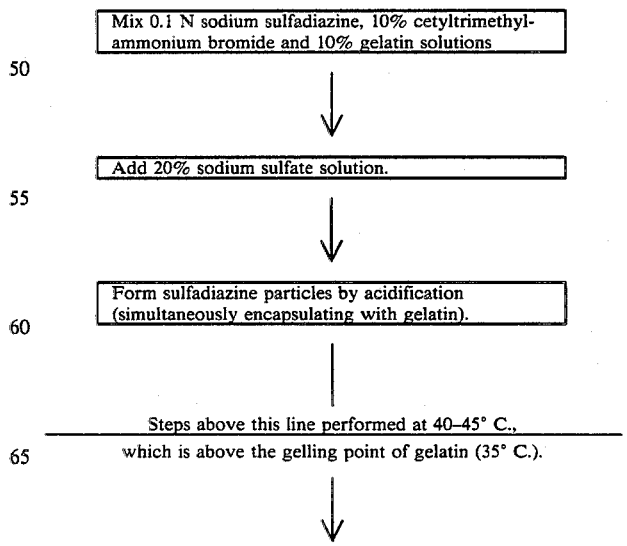

```
Gel the encapsulating material by pouring the
suspension into cold (5° C.) sodium sulfate solution.
```
```
Collect the microcapsules by centrifugation.
```

According to a third embodiment of the invention, the process comprises the following steps which are carried out at room temperature.

(a) mixing a solution of a suitable pharmaceutically active compound and sodium lauryl sulfate;

(b) adding methylcellulose and sodium carbomethylcellulose solutions to the mixture obtained in step a;

(c) adding sodium sulfate solution to the solution obtained in step b; and (d) titrating the solution obtained in step c with a suitable acid or base titrant while keeping the solution under constant agitation which results in a suspension of encapsulated pharmaceutically active small particles and coacervation of the gelatin.

The suspension is then poured into a cold sodium sulfate solution and stirred at the temperature of an ice bath. This procedure causes "hardening" of the liquid methyl cellulose/carboxymethylcellulose shell of the microcapsules. The microcapsules are then collected, for instance, by centrifugation.

The ratio of pharmaceutically active compounds to sodium lauryl sulfate is about 1:(0.5–1). In step b preferably 1% aqueous solution of methylcellulose and carboxymethylcellulose and in step c preferably a 20% aqueous solution of sodium sulfate is used.

EXAMPLE 3

An aqueous solution consisting of 10 ml of 0.1N sodium sulfadiazine (27.2 g/l) and 0.5 g of sodium lauryl sulfate was mixed at room temperature (25° C.) under constant agitation at medium speed using a magnetic stirrer, until the solution became clear. Two sequential additions were then made, each of which was followed by stirring:

(1) 10 ml each of 1% methylcellulose (400 cps) and 1% sodium carboxymethylcellulose (medium viscosity) with stirring for 3 minutes, and (2) 4 ml of 20% sodium sulfate with stirring for an additional 3 minutes. With continued stirring at a fast rate, 10 ml of 0.1N hydrochloric acid solution was added from a fully opened buret.

The resulting white suspension of microencapsulated sulfadiazine particles were stirred for an additional 10 minutes. The microcapsules were "hardened" by pouring the suspensions into 200 ml of cold (5° C.) 7% sodium sulfate solution and stirred at medium speed for 30 minutes at the temperature of ice bath. According to microscopic inspection, the microcapsules were of a size less than 10 μm. The entire procedure is outlined in the diagram below:

```
Mix 0.1 N sodium sulfadiazine solution and 0.5 g
sodium lauryl sulfate.
```

```
Add 1% methylcellulose and 1% sodium carboxy-
methylcellulose solutions.
```
```
Add 20% sodium sulfate solution.
```
```
Form sulfadiazine particles by acidification
(simultaneously encapsulating with methyl-
cellulose/carboxymethylcellulose).
```
```
Gel the encapsulating material by pouring the
suspension into cold (5° C.) sodium sulfate solution.
```
```
Collect the microcapsules by centrifugation
```

According to a fourth embodiment of the invention, the process comprises the following steps which are carried out at room temperature.

(a) mixing solutions of a suitable pharmaceutically active compound and cellulose acetate phthalate;

(b) adding a sodium sulfate solution to the mixture obtained in step a; and (c) titrating the solution obtained in step b with a suitable acid or base titrant while being kept under constant agitation which results in a suspension of encapsulated pharmaceutically active small particles and coacervation of the cellulose acetate phthalate.

The suspension is then poured into cold sodium sulfate solution and stirred at the temperature of an ice bath. This procedure causes "hardening" of the liquid cellulose acetate phthalate shell of the microcapsules. The microcapsules are then collected, for instance, by centrifugation.

The ratio of pharmaceutically active compound: cellulose acetate phthalate is 3:1. In step b, preferably a 20% aqueous solution of sodium sulfate is used.

EXAMPLE 4

An aqueous solution consisting of 10 ml of 0.1N sodium sulfadiazine (27.2 g/l) and 10 ml of alkaline (0.1M NaOH) 1% cellulose acetate phthalate (Eastman 4642) was stirred at medium speed with a magnetic stirrer until homogenous. 10 ml of 20% sodium sulfate was then added and the solution stirred for an additional 10 minutes. The last step was the rapid addition of 10 ml of 0.1N hydrochloric acid from a fully opened buret while the solution was under constant fast agitation with the magnetic stirrer. The resulting suspension of microencapsulated sulfadiazine was stirred for an additional 10 minutes. The microcapsules were "hardened" by pouring the suspensions into 200 ml of cold (5° C.) 7% sodium sulfate solution and stirred at medium speed for 30 minutes at the temperature of an ice bath.

According to microscopic inspection, the microcapsules were of a size less than 10 μm. The entire procedure is outlined in the diagram below:

```
Mix 0.1 N sodium sulfadiazine and 1% cellulose
acetate phthalate solutions.
                    ↓
Add 20% sodium sulfate solution
                    ↓
Form sulfadiazine particles by acidification
(simultaneously encapsulating with cellulose
acetate phthalate).
                    ↓
Gel the encapsulating material by pouring the
suspension into cold (5° C.) sodium sulfate solution.
                    ↓
Collect the microcapsules by centrifugation
```

According to the fifth embodiment of the invention, the process comprises the following steps which are performed at 60° C.

(a) dissolving sodium sulfate in an aqueous solution of a suitable pharmaceutically active compound;

(b) adding a solution of polyvinylpyrrolidone to the solution obtained in step a;

(c) adding a solution of sodium sulfate to the solution obtained in step b; and (d) titrating the solution obtained in step c with a suitable acid or base titrant while keeping the solution under constant agitation which results in a suspension of encapsulated pharmaceutically active small particles and coacervation of the polyvinyl pyrrolidone.

The suspension is then poured into cold sodium sulfate solution and stirred at the temperature of an ice bath. This procedure causes "hardening" of the liquid polyvinylpyrrolidone shell of the microcapsules. The microcapsules are then collected, for instance, by centrifugation.

The ratio of pharmaceutically active compound: sodium sulfate is 1:4.

In step b, preferably a 20% aqueous solution of sodium sulfate is used.

The sodium sulfate solution to which the suspension of particles is added should have a strength of about 7% and its temperature should be below 15° C., preferably in the temperature range 0°–15° C.

EXAMPLE 5

A solution consisting of 10 ml of 0.1N sodium sulfadiazine (27.2 g/l) and 1 g of sodium sulfate was prepared by heating to 60° C. while under constant agitation at medium speed with a magnetic stirrer. The solution was then maintained at 60° C., 10 ml of 2% polyvinylpyrrolidone (average molecular weight, 360,000) was added, the solution stirred for 3 minutes. The stirring speed was changed to fast and 10 ml of 0.1N hydrochloric acid solution added from an open buret. The white suspension of microcapsules were stirred for 10 minutes.

The microcapsules were "hardened" by pouring the suspensions into 200 ml of cold (5° C.) 7% sodium sulfate solution and stirred at medium speed for 30 minutes at icebath temperature. According to microscopic inspection, the microcapsules were of a size less than 10 μm. The entire procedure is outlined in the diagram below:

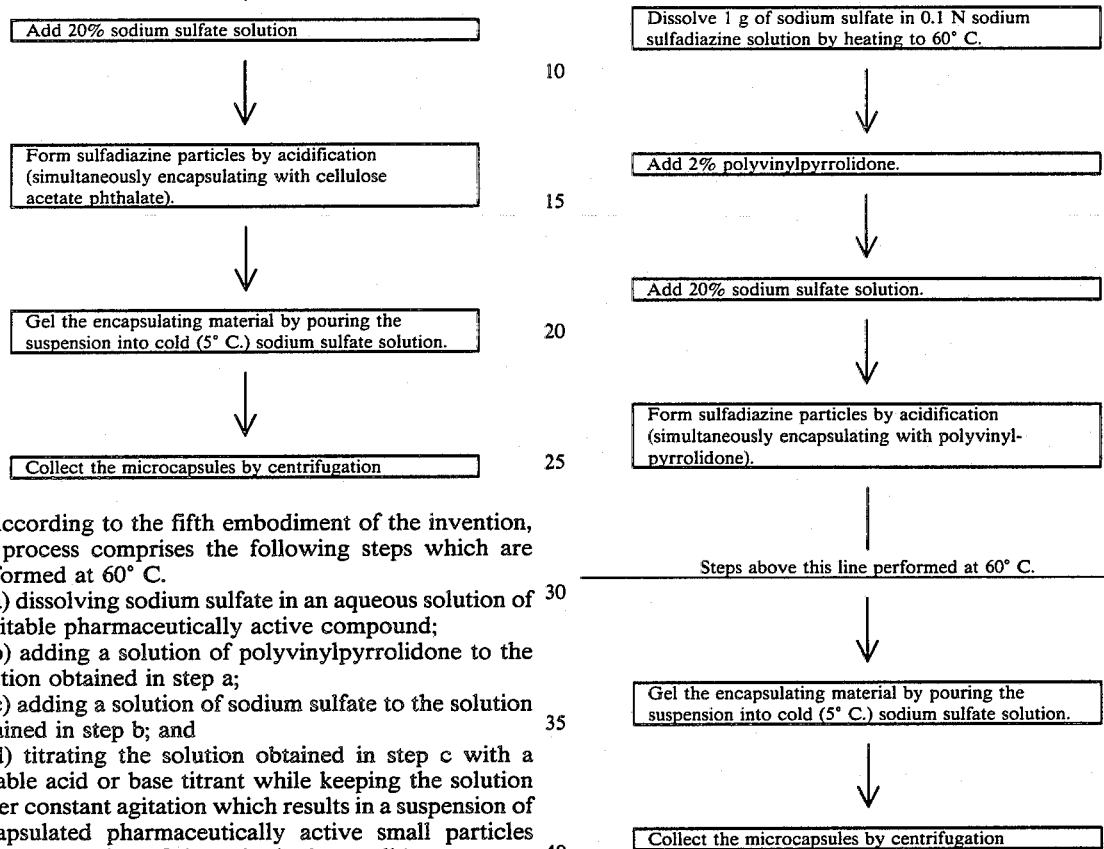

According to the sixth embodiment, the process comprises the following steps which are carried out at a temperature above 35° C., preferably 38° C.

(a) dissolving gelatin in water;

(b) adding sodium sulfate to the solution from step a;

(c) adding a suitable pharmaceutically active compound in the solution from step b;

(d) adding a sodium hydroxide solution or other alkaline solution, for example, potassium hydroxide, or adding a hydrochloric acid solution or other acidic solution, for example, acetic acid, to the solution from step c; and (e) titrating the solution obtained in step (d) with a suitable amount of acid or base titrant while keeping the solution under constant agitation which results in a suspension of encapsulated pharmaceutically active small particles and coacervation of the gelatin; and (f) the suspension is then poured into cold sodium sulfate solution and stirred at the temperature of an ice bath to cause "gelling" of the liquid gelatin shell of the microcapsules, and the microcapsules are collected, for instance, by centrifugation; or (g) the suspension in cold sodium sulfate solution is centrifuged and washed twice with water, centrifuged, dispersed into water, formaldehyde solution added under stirring and the suspension allowed to stand at room temperature. This procedure causes hardening of the gelled microcapsule shell. The suspension is centrifuged, the mirocapsules washed twice with water, redispersed in water with stirring, isopropanol added, filtered, washed twice with isopropanol, filtered and dried. This procedure causes dehydration of the hardened microcapsules. Alternatively the mirocapsules from step f collected directly, for instance, by centrifugation, are redispersed in cold water (5° C.), a solution consisting of formaldehyde and isopropanol is added, the suspension allowed to stand at room temperature, and then collected, for instance, by centrifugration. The ratio of pharmaceutically active compound to sodium sulfate is, for example, 1:2. The gelatin solution should preferably be prepared from type B (acid processed) gelatin, and of a pharmaceutical grade. The gelatin should be added as a 2-10% (w/w) solution, preferably a 5% (w/w) solution. The formaldehyde should be added as a 5-37% (w/w) solution, preferably a 37% (w/w) solution. The alcohol can be any water-miscible alcohol, preferably isopropanol, and the mixture with water can be 5-50% (w/w) isopropanol. Alternatively, a formaldehyde-alcohol mixture can be used as a 1:5-30 (v/v) mixture (formaldehyde, 38%:alcohol), preferably a 1:19 (v/v) mixture (formaldehyde, 38%:isopropanol).

EXAMPLE 6

A solution consisting of 0.34 g of gelatin (type B: acid processed) in 20 ml of water was prepared, 1.34 g of sodium sulfate was added, followed by 1.0 g of 9-(3,4-dihydroxybutyl)guanine and then by 1.0 ml of 5.0N sodium hydroxide solution, and the resulting solution was titrated while under constant agitation with a magnetic stirrer, with 0.95 ml of 5.0N hydrochloric acid solution. This procedure resulted in a white suspension of microencapsulated 9-(3,4-dihydroxybutyl)guanine particles. The suspension was then stirred at 38° C. for 3 minutes and then at room temperature for an additional 20 minutes, following which the microcapsules were collected by centrifugaaion. The microcapsules were redispersed into 0.5 ml of cold water, 20 ml of a solution consisting of formaldehyde solution 38%, and isopropanol in the ratio of 1:19 (v/v) was added under stirring and the suspension allowed to stand at room temperature for 15-20 hours. The suspension was centrifuged and the microcapsules collected and dried in a low pressure oven at 35° C.

---

Mix 1.7% gelatin solution with 6.7% sodium sulfate and 5% 9-(3,4-dihydroxybutyl)-guanine.

Add 5% 5 N sodium hydroxide solution.

Form 9-(3,4-dihydroxybutyl)-guanine particles by acidification (simultaneously encapsulating with gelatin).

Steps above this line performed at 38° C., which is above the gelling point of gelatin (35° C.)

-continued

Harden the encapsulating material and dehydrate the microcapsules by adding a solution of formaldehyde in isopropanol.

Collect the microcapsules by centrifugation.

We claim:

1. A process for encapsulating a weakly acidic organic compound whose solubility in water is greater at a first pH than at a second pH which process comprises:
   (a) dissolving said compound in water in the presence of sufficient base to raise the pH to said first pH and at least 2 pH units above the pKa of the compound, together with an encapsulating material and an electrolyte which is effective, but present in an amount just insufficient to cause coacervation of the encapsulating material without interacting with it;
   (b) stirring and titrating the solution with a titrant effective to reduce the pH of said solution to said second pH to cause the concurrent precipitation of the compound as small particles and formation of a coacervate of the encapsulating material; and
   (c) gelling the encapsulating material.

2. A process according to claim 1, wherein the pharmaceutically active compound is selected from the group consisting of bacampicillin, griseofulvin, indomethacin, sodium sulfadiazine, erythromycin, theophylline, salicylic acid, acetylsalicylic acid, chlorozoxazone, lidocaine and alaproclate.

3. A process according to claim 1, wherein the encapsulating material is selected from the group consisting of gelatin, methylcellulose, sodium carboxymethylcellulose, cellulose acetate phthalate, and polyvinylpyrrolidone.

4. A process for encapsulating a weakly basic organic compound whose solubility in water is greater at a first pH than at a second pH which process comprises:
   (a) dissolving said compound in water in the presence of sufficient acid to lower the pH to said first pH and at least 2 pH units below the pKa of the compound, together with an encapsulating material and an amount of an electrolyte which is effective, but just insufficient to cause coacervation of the encapsulating material without interacting with it;
   (b) stirring and titrating the solution with a titrant effective to raise the pH of said solution to said second pH to cause the concurrent precipitation of the compound as small particles and formation of a coacervate of the encapsulating material; and
   (c) gelling the encapsulating material.

5. A process according to claim 4 wherein the compound is sulfadiazine in sodium sulfate solution containing ethyl alcohol and the encapsulating material is a gelatin solution.

6. A process according to claim 5, wherein the ratio of compound to encapsulating material to wetting agent to electrolyte is about (0.1-6):(0.1-4):(0.1-10):(0.4-48).

7. A process according to claims 1 or 4 wherein the compound is pharmaceutically active.

8. The process according to claim 7 wherein the first pH is an acid pH.

9. A process according to claim 1 or 4 wherein a wetting agent is used in step a.

10. A process according to claim 1 or 4 wherein, if needed, the temperature is controlled in step b.

* * * * *